(12) United States Patent
Segal et al.

(10) Patent No.: US 11,592,407 B2
(45) Date of Patent: Feb. 28, 2023

(54) SYSTEMS, DEVICES, AND METHODS FOR X-RAY FLUORESCENCE ANALYSIS OF GEOLOGICAL SAMPLES

(71) Applicant: Enersoft Inc., Calgary (CA)

(72) Inventors: Yannai Z. R. Segal, Calgary (CA); Grant I. Sanden, Calgary (CA)

(73) Assignee: Enersoft Inc., Calgary (CA)

( * ) Notice: Subject to any disclaimer, the term of this patent is extended or adjusted under 35 U.S.C. 154(b) by 0 days.

(21) Appl. No.: 17/056,110

(22) PCT Filed: May 17, 2019

(86) PCT No.: PCT/CA2019/000072
§ 371 (c)(1),
(2) Date: Nov. 17, 2020

(87) PCT Pub. No.: WO2019/218051
PCT Pub. Date: Nov. 21, 2019

(65) Prior Publication Data
US 2021/0208089 A1    Jul. 8, 2021

Related U.S. Application Data

(60) Provisional application No. 62/673,507, filed on May 18, 2018.

(51) Int. Cl.
*G01N 23/22*      (2018.01)
*G01N 23/2204*   (2018.01)
(Continued)

(52) U.S. Cl.
CPC ....... *G01N 23/223* (2013.01); *G01N 23/2204* (2013.01); *G01N 23/2206* (2013.01);
(Continued)

(58) Field of Classification Search
CPC .............. G01N 23/22; G01N 23/2204; G01N 23/2206; G01N 23/2208; G01N 23/223;
(Continued)

(56) References Cited

U.S. PATENT DOCUMENTS 3,889,113 A * 6/1975 Rhodes ................ G01N 23/223
                                                             378/45
4,852,135 A * 7/1989 Anisovich ............ G01N 23/223
                                                             378/45

(Continued)

OTHER PUBLICATIONS

ISA/CA, International Search Report and Written Opinion, dated Aug. 27, 2019, re PCT International Patent Application No. PCT/CA2019/000072.

*Primary Examiner* — Allen C. Ho
(74) *Attorney, Agent, or Firm* — Ridout & Maybee LLP

(57) ABSTRACT

A geological analysis system, device, and method are provided. The geological analysis system includes sensors, including an X-ray fluorescence (XRF) unit, which detect properties of geological sample materials, a sample tray which holds the geological sample materials therein, and a processor. The XRF unit includes a body and a separable head unit and an output port configured to emit helium onto the geological sample materials within the sample tray. The sample tray includes chambers formed in an upper surface, ports, and passages, each providing communication between an interior of a chamber and an interior of a port. The ports are configured to be attachable to vials. The processor is configured to automatically position at least one of the sensors and the sample tray with respect to the other of the at least one of the sensors and the sample tray and to control the sensors.

13 Claims, 7 Drawing Sheets

(51) Int. Cl.
    *G01N 23/223* (2006.01)
    *G01N 33/24* (2006.01)
    *G01N 23/2206* (2018.01)
    *G01N 23/2208* (2018.01)
(52) U.S. Cl.
    CPC ....... *G01N 23/2208* (2013.01); *G01N 33/241* (2013.01); *G01N 2223/076* (2013.01); *G01N 2223/507* (2013.01); *G01N 2223/616* (2013.01)
(58) Field of Classification Search
    CPC ....... G01N 2223/076; G01N 2223/507; G01N 2223/616
    USPC ...................................... 378/44–50
    See application file for complete search history.

(56) References Cited

U.S. PATENT DOCUMENTS

| | | | | |
|---|---|---|---|---|
| 5,107,527 A * | 4/1992 | Sipila | G01N 23/20083 | 378/46 |
| 5,187,727 A * | 2/1993 | Vogler | G01N 23/223 | 378/50 |
| 5,325,416 A * | 6/1994 | Saito | G01N 23/223 | 378/50 |
| 5,657,363 A * | 8/1997 | Hossain | G01N 23/223 | 378/45 |
| 5,712,891 A * | 1/1998 | Benony | G01N 23/223 | 378/45 |
| 5,721,759 A * | 2/1998 | Raatikainen | G01N 23/223 | 378/47 |
| 5,742,658 A * | 4/1998 | Tiffin | G01N 23/20 | 257/E21.53 |
| 5,832,054 A * | 11/1998 | Kuwabara | G01N 23/223 | 378/80 |
| 5,937,026 A * | 8/1999 | Satoh | G01N 23/223 | 378/45 |
| 6,052,429 A * | 4/2000 | Ohno | G01N 23/223 | 378/45 |
| 6,108,398 A * | 8/2000 | Mazor | G01N 23/223 | 379/49 |
| 6,233,307 B1 * | 5/2001 | Golenhofen | G01N 23/223 | 714/E11.21 |
| 6,266,390 B1 * | 7/2001 | Sommer, Jr | G01N 23/223 | 378/45 |
| 6,292,532 B1 * | 9/2001 | Kawahara | G01N 23/223 | 378/45 |
| 6,295,333 B1 * | 9/2001 | Tamura | G01N 23/223 | 378/50 |
| 6,314,158 B1 * | 11/2001 | Shiota | G01N 23/223 | 378/49 |
| 6,345,086 B1 * | 2/2002 | Ferrandino | G01N 23/223 | 378/206 |
| 6,370,220 B1 * | 4/2002 | Stoop | G01N 23/223 | 378/50 |
| 6,381,303 B1 * | 4/2002 | Vu | G01N 23/20 | 378/46 |
| 6,400,795 B2 * | 6/2002 | Yagi | G01N 23/223 | 378/45 |
| 6,421,415 B1 * | 7/2002 | Peczkis | G01N 23/2206 | 378/53 |
| 6,426,993 B1 * | 7/2002 | Satoh | G01N 23/223 | 378/45 |
| 6,453,002 B1 * | 9/2002 | Mazor | G01N 23/223 | 378/49 |
| 6,477,227 B1 * | 11/2002 | Kaiser | G01N 23/223 | 378/45 |
| 6,512,810 B1 * | 1/2003 | Haszler | G01B 15/02 | 378/50 |
| 6,522,718 B2 * | 2/2003 | Sato | G01B 15/02 | 378/50 |
| 6,577,705 B1 * | 6/2003 | Chang | G01N 23/223 | 378/45 |
| 6,697,454 B1 * | 2/2004 | Nicolich | G21K 1/06 | 378/48 |
| 6,754,304 B1 * | 6/2004 | Kumakhov | G01N 23/223 | 378/45 |
| 6,810,106 B2 * | 10/2004 | Sato | G01N 23/223 | 378/50 |
| 6,823,041 B2 * | 11/2004 | Greenbank | G01N 23/20025 | 378/208 |
| 6,826,253 B2 * | 11/2004 | Greenbank | G01N 23/20 | 378/208 |
| 6,850,592 B2 * | 2/2005 | Schramm | G01N 23/223 | 162/57 |
| 7,020,238 B1 * | 3/2006 | Kantonen | G01N 23/223 | 378/102 |
| 7,065,174 B2 * | 6/2006 | Sipilä | G01N 23/223 | 378/45 |
| 7,233,643 B2 * | 6/2007 | Sipilä | G01N 23/223 | 378/45 |
| 7,277,527 B2 * | 10/2007 | Gallagher | G01N 33/2835 | 378/47 |
| 7,298,817 B2 * | 11/2007 | Chen | G01N 23/223 | 378/47 |
| 7,342,995 B2 * | 3/2008 | Sato | G01N 23/20 | 378/46 |
| 7,356,114 B2 * | 4/2008 | Kataoka | G01B 15/02 | 378/50 |
| 7,375,359 B1 * | 5/2008 | Grodzins | G01N 23/223 | 378/45 |
| 7,409,037 B2 * | 8/2008 | Puusaari | G01N 23/223 | 378/45 |
| 7,424,093 B2 * | 9/2008 | Fukai | G01N 23/223 | 378/208 |
| 7,428,293 B2 * | 9/2008 | Fukai | G01N 23/223 | 378/46 |
| 7,430,273 B2 * | 9/2008 | Yellepeddi | G01N 21/67 | 378/45 |
| 7,430,274 B2 * | 9/2008 | Connors | G01N 23/223 | 378/102 |
| 7,436,926 B2 * | 10/2008 | Matoba | G01N 23/223 | 378/45 |
| 7,440,541 B2 * | 10/2008 | Hubbard-Nelson | G01N 33/287 | 378/45 |
| 7,443,951 B2 * | 10/2008 | Kenning | G01N 23/223 | 378/102 |
| 7,515,685 B2 * | 4/2009 | Iwamoto | G01N 23/223 | 378/79 |
| 7,535,989 B2 * | 5/2009 | Russell | G01N 23/223 | 378/79 |
| 7,587,025 B2 * | 9/2009 | Fukai | G01N 23/223 | 378/86 |
| 7,623,621 B1 * | 11/2009 | Schramm, Jr. | G01N 23/223 | 378/44 |
| 7,623,625 B2 * | 11/2009 | Boyden | G01N 23/201 | 378/86 |
| 7,627,088 B2 * | 12/2009 | Matoba | H01J 35/186 | 378/45 |
| 7,634,053 B2 * | 12/2009 | Matoba | G01N 23/223 | 378/47 |
| 7,634,054 B2 * | 12/2009 | Matoba | H01J 35/186 | 378/46 |
| 7,653,174 B2 * | 1/2010 | Mazor | G01N 23/223 | 378/50 |
| 7,680,243 B2 * | 3/2010 | Yokhin | G01N 23/2206 | 378/45 |
| 7,680,248 B2 * | 3/2010 | Matoba | H01J 35/186 | 378/140 |
| 7,688,942 B2 * | 3/2010 | Klein | G01N 23/223 | 250/400 |
| 7,763,820 B1 * | 7/2010 | Sommer, Jr | B07C 5/346 | 209/576 |
| 7,796,726 B1 * | 9/2010 | Gendreau | G01N 23/223 | 378/46 |
| 7,916,834 B2 * | 3/2011 | Piorek | G01N 23/223 | 378/102 |

(56) References Cited

U.S. PATENT DOCUMENTS

| | | | | |
|---|---|---|---|---|
| 7,970,101 B2* | 6/2011 | Sakai | G01N 23/223 | 378/46 |
| 7,978,820 B2* | 7/2011 | Kharchenko | G01N 23/2206 | 378/70 |
| 7,983,386 B2* | 7/2011 | Yellepeddi | G01N 23/223 | 378/70 |
| 8,000,439 B2* | 8/2011 | Matoba | G01N 23/223 | 378/45 |
| 8,064,570 B2* | 11/2011 | Tannian | G01N 23/223 | 378/45 |
| 8,068,583 B2* | 11/2011 | Matoba | G01N 23/223 | 378/90 |
| 8,155,268 B2* | 4/2012 | Pesce | G01N 23/223 | 378/45 |
| 8,229,064 B2* | 7/2012 | Grodzins | G01N 23/223 | 378/45 |
| 8,380,541 B1 | 2/2013 | Holmes | | |
| 8,408,789 B2* | 4/2013 | Takahara | G01N 23/223 | 378/206 |
| 8,494,113 B2* | 7/2013 | Grodzins | G01T 1/00 | 378/45 |
| 8,548,121 B2* | 10/2013 | Sakai | G01N 23/223 | 378/44 |
| 8,550,710 B2* | 10/2013 | Kishida | G01N 23/223 | 378/45 |
| 8,582,717 B2* | 11/2013 | Ohzawa | G01N 23/223 | 378/45 |
| 8,611,493 B2* | 12/2013 | Hasegawa | G01N 23/223 | 378/44 |
| 8,693,625 B2* | 4/2014 | Dugas | G01N 23/223 | 378/45 |
| 8,787,523 B2* | 7/2014 | Sackett | G01N 23/223 | 378/117 |
| 8,835,857 B2* | 9/2014 | Eggert | G01T 7/00 | 378/53 |
| 8,855,809 B2* | 10/2014 | Spencer | B07C 5/3416 | 700/223 |
| 9,057,685 B2* | 6/2015 | Allen | H01J 35/16 | |
| 9,415,392 B2 | 8/2016 | Ismagilov et al. | | |
| 9,810,649 B2* | 11/2017 | Takahara | G21F 3/00 | |
| 10,207,296 B2* | 2/2019 | Garcia | B07C 5/34 | |
| 10,247,683 B2* | 4/2019 | Yun | G01N 23/2055 | |
| 10,295,486 B2* | 5/2019 | Yun | G01N 23/20058 | |
| 10,473,598 B2* | 11/2019 | Ogata | G01N 23/203 | |
| 10,634,628 B2* | 4/2020 | Kasper | H01L 21/68764 | |
| 10,800,315 B2* | 10/2020 | Kanck | B60P 3/14 | |
| 10,823,688 B2* | 11/2020 | Akiyama | G01N 23/223 | |
| 10,948,435 B2* | 3/2021 | Furukawa | G01N 23/223 | |
| 11,320,384 B2* | 5/2022 | Grof | G06K 19/06009 | |
| 2017/0074652 A1 | 3/2017 | Send et al. | | |

* cited by examiner

SYSTEMS, DEVICES, AND METHODS FOR X-RAY FLUORESCENCE ANALYSIS OF GEOLOGICAL SAMPLES

CROSS-REFERENCE TO RELATED APPLICATION(S)

This application claims the benefit of U.S. provisional Application 62/673,507 filed May 18, 2018 in the United States Patent and Trademark Office, the disclosure of which is incorporated herein by reference in its entirety. Applicant also incorporates herein by reference the entirety of the disclosure of U. S. Publication 2014/0379317, filed on Jun. 25, 2014 in the U.S. Patent and Trademark Office as U.S. application Ser. No. 14/314,791.

BACKGROUND

1. Field

Apparatuses and methods consistent with exemplary embodiments relate to analysis of soil and other geological samples, using x-ray fluorescence (XRF) and spectroscopy, among other techniques, and, more specifically to systems, devices, and methods according to which multiple analysis techniques may be applied to the samples simultaneously, or in close sequence.

2. Description of the Related Art

Hydrocarbon exploration, geothermal evaluation, and other applications involving subsurface geostatistics often involve large volumes of data and numerous techniques and parameters for modeling geostatistical information. This data can include many combination(s) and permutations of enterprise, geological, and geostatistical data, which may be generated, stored, and or made available by large and diverse numbers of public, private, academic, and government sources.

Development of unconventional resources can require accurate placement of well paths in highly adverse or sensitive environments, for example, placement of horizontal/directional well paths within vertically narrow zones containing both high saturation of hydrocarbons and geological properties favorable to production, such as fracture propagation. Target zones can be identified via analysis of cored exploration wells, seismic surveys of structure, and other methods, but can only be estimated throughout the reservoir for purposes of well planning. Therefore, even if the well bore position can be accurately assessed, the determination of actual geological properties during drilling are required to be determined if the planned path is actually in the target zone. Related art measurement-while-drilling geosteering methods using downhole logs may be insufficient for differentiating between target and non-target zones because they are limited to measuring proxy characteristics such as resistivity and passive gamma radiation, which may not differ between target zones and adjacent zones.

Parameters of interest may be measureable directly from geological cuttings. Related art wellsite geology involves subjective visual analysis of cuttings which may not accurately distinguish target zones from non-target zones. Related art measurement methods for cuttings may be slow and expensive, potentially requiring sample preparation and lengthy analyses to detect properties of interest, along with manual data entry, transfer, and aggregation to obtain usable results. This process may not be time- or cost-effective, even for retroactively determining well placement accuracy, as a typical sampling collection rate of one sample per five meters generates over 500 samples for a typical 2500 meter horizontal well. Related art methods may be incapable of throughput matching a drilling rate of up to six samples per hour.

An XRF spectrometer is an x-ray instrument used for routine, relatively non-destructive chemical analyses of rocks, minerals, sediments, and fluids. It works on wavelength-dispersive spectroscopic principles that are similar to an electron microprobe (EPMA). However, an XRF spectrometer cannot generally make analyses at the small spot sizes typical of EPMA work (about 2-5 microns), so it is typically used for bulk analyses of larger fractions of geological materials. The relative ease and low cost of sample preparation, and the stability and ease of use of X-ray spectrometers make this one of the most widely used methods for analysis of major and trace elements in rocks, minerals, and sediment.

XRF methods depend on fundamental principles that are common to several other instrumental methods involving interactions between electron beams and X-rays with samples, including X-ray spectroscopy (e.g., scanning electron microscopy/energy dispersive x-ray spectroscopy (SEM-EDS)), X-ray diffraction (XRD), and wavelength dispersive spectroscopy (microprobe WDS).

The analysis of major and trace elements in geological materials by XRF is made possible by the behavior of atoms when they interact with radiation. When materials are excited with high-energy, short wavelength radiation (e.g., X-rays), they can become ionized. If the energy of the radiation is sufficient to dislodge a tightly-held inner electron, the atom becomes unstable and an outer electron replaces the missing inner electron. When this happens, energy is released due to the decreased binding energy of the inner electron orbital compared with an outer one. The emitted radiation is of lower energy than the primary incident X-rays and is termed fluorescent radiation. Because the energy of the emitted photon is characteristic of a transition between specific electron orbitals in a particular element, the resulting fluorescent X-rays can be used to detect the abundances of elements that are present in the sample.

An XRF spectrometer works because if a sample is illuminated by an intense X-ray beam, known as the incident beam, some of the energy is scattered, but some is also absorbed within the sample in a manner that depends on its chemistry. The incident X-ray beam is typically produced from a Rh target, although W, Mo, Cr and others can also be used, depending on the application.

When this primary X-ray beam illuminates the sample material, the material is said to be excited. The excited material in turn emits X-rays along a spectrum of wavelengths characteristic of the types of atoms present in the material. The atoms in the material absorb X-ray energy by ionizing, ejecting electrons from the lower (usually K and L) energy levels. The ejected electrons are replaced by electrons from an outer, higher energy orbital. When this happens, energy is released due to the decreased binding energy of the inner electron orbital compared with an outer one. This energy release is in the form of emission of characteristic X-rays indicating the type of atom present. If a material has many elements present, as is typical for most minerals and rocks, the use of a Wavelength Dispersive Spectrometer much like that in an EPMA allows the separation of a complex emitted X-ray spectrum into characteristic wavelengths for each element present. Various types of detectors (gas flow proportional and scintillation) are used to measure the intensity of the emitted beam. The flow counter is commonly utilized for measuring long wavelength (>0.15 nm) X-rays that are typical of K spectra from elements lighter than Zn. The scintillation detector is commonly used to analyze shorter wavelengths in the X-ray spectrum (K spectra of element from Nb to I; L spectra of Th and U). X-rays of intermediate wavelength (K spectra produced from Zn to Zr and L spectra from Ba and the rare earth elements) are generally measured by using both detectors in tandem. The intensity of the energy measured by these detectors is proportional to the abundance of the element in the sample material. The exact value of this proportionality for each element is derived by comparison to mineral or rock standards whose composition is known from X-ray fluorescence is somewhat limited to analysis of relatively large samples, typically >1 gram; materials that can be prepared in a powder form and effectively homogenized; materials for which compositionally similar, well-characterized standards are available; and materials containing high abundances of elements for which absorption and fluorescence effects are reasonably well understood.

In most cases of rocks, ores, sediments and minerals, the sample material is ground to a fine powder. At this point it may be analyzed directly, especially in the case of trace element analyses. However, the very wide range in abundances of different elements, especially iron, and the wide range of sizes of grains in a powdered material, makes the proportionality comparison to the standards particularly troublesome. For this reason, it is related art practice to mix the powdered material with a chemical flux and use a furnace or gas burner to melt the powdered material. Melting creates a homogenous glass that can be analyzed and the abundances of the (now somewhat diluted) elements can be calculated.

In view of these features, XRF is particularly well-suited for investigations that involve bulk chemical analyses of major elements (Si, Ti, Al, Fe, Mn, Mg, Ca, Na, K, P) in rock and sediment; and bulk chemical analyses of trace elements (>1 ppm; Ba, Ce, Co, Cr, Cu, Ga, La, Nb, Ni, Rb, Sc, Sr, Rh, U, V, Y, Zr, Zn) in rock and sediment. In theory XRF has the ability to detect X-ray emission from virtually all elements, depending on the wavelength and intensity of incident x-rays. However, in practice, most commercially-available instruments are very limited in their ability to precisely and accurately measure the abundances of elements with Z<11 in most natural earth materials. Related art XRF analyses cannot distinguish variations among isotopes of an element, so these analyses are routinely done with other processes, such as thermal ionization mass spectrometry (TIMS) and secondary ion mass spectrometry (SIMS). Furthermore, XRF analyses cannot distinguish ions of the same element in different valence states, so these analyses of rocks and minerals are done with techniques such as wet chemical analysis or Mossbauer spectroscopy.

Virtually any solid or liquid material can be analyzed, if adequate standards are available. For rocks and minerals, related art commercial instruments require a sample constituting at least several grams of material, although the sample collected may be much larger. For XRF chemical analyses of rocks, samples are collected that are several times larger than the largest size grain or particle in the rock. This initial material then suffers a series of crushing steps to reduce it to an average grain size of a few millimeters to a centimeter, when it can be reduced by splitting to a small representative sample of a few tens to hundreds of grams. This small sample split is then ground into a fine powder by any of a variety of techniques to create the XRF sample material. Care must be taken particularly at this step to be aware of the composition of the crushing implements, which will inevitably contaminate the material to some extent.

In view of the above, there is a need in the art for a system and method of obtaining relevant data from samples more quickly and efficiently for use in real-time in the field.

SUMMARY

Exemplary embodiments may address at least the above problems and/or disadvantages and other disadvantages not described above. Also, exemplary embodiments are not required to overcome the disadvantages described above, and may not overcome any of the problems described above.

Exemplary embodiments may provide robotics capable of accurately positioning samples so that multiple sensors can quickly measure the same precise points. By directly integrating with sensor technologies spanning the electromagnetic spectrum, one or more exemplary embodiments may be capable of determining atomic composition, molecular composition, and structure. Through direct control and purpose-built engineering improvements, of a variety of sensor types, one or more exemplary embodiments may achieve measurements otherwise unattainable from non-destructive, non-prepped testing, including detection of sodium and magnesium, imaging down to nanometer resolution, and sub-mm mineralogical/saturation mapping. Thus, according to one of more exemplary embodiments, possible resultant data sets may result in a large volume of high-resolution and high-meaningful-degrees-of-freedom data sets directly tied to all aspects of geological composition.

One or more exemplary embodiments may provide a system of geoscience technologies enabling a methodology of assessing directional well placement leading to a geosteering solution.

One or more exemplary embodiments may provide a system of geoscience technologies enabling an accelerated and improved data collection from geological samples, and the ability to go from data to decision in time to affect drilling decisions.

According to an aspect of an exemplary embodiment, a geological analysis system comprises: at least one frame; a plurality of sensors each mounted on the at least one frame. The plurality of sensors may include an X-ray fluorescence (XRF) sensor comprising an X-ray emitter and an X-ray fluorescence detector. The system further includes a sample tray having a plurality of concave chambers formed therein. The sample tray is positionable in a first analysis position with respect to the XRF sensor such that a geological sample material disposed in one of the plurality of concave chambers is irradiated by X-ray radiation emitted from the X-ray emitter. The sample tray is positionable in a second analysis position with respect to a second sensor in the plurality of sensors such that the second sensor in the plurality of sensors may obtain data regarding the geological sample material. The system further includes a processor configured to: control a position of at least one of the sample tray and the plurality of sensors; control operation of the plurality of sensors; output data received from the plurality of sensors; and effect semi-automatic or fully-automatic robotic positioning of one or both of the sample tray and the plurality of sensors with respect to the other.

According to an aspect of another exemplary embodiment, a sample tray is configured to hold geologic samples for analysis, and includes a plurality of concave chambers formed in an upper surface thereof; a plurality of ports; and a plurality of passages, each of the plurality of passages providing a passage in communication between an interior of one of the plurality of chambers and an interior of one of the plurality of ports. Each of the plurality of passages forms an angle with respect to the upper surface of the tray, such that material disposed within one of the plurality of chambers is maintained within the chamber when the tray is positioned such that the upper surface is substantially horizontal and such that the material disposed within the one of the plurality of chambers is transferred, via an associated opening of the plurality of openings, into an associated port of the plurality of ports, when the tray is positioned such that the upper surface is angled with respect to horizontal. Each of the plurality of ports is configured to attach to a vial, such that a seal between the vial and the port may be maintained by friction therebetween.

According to an aspect of another exemplary embodiment, an X-ray fluorescence (XRF) unit includes a body; and a head configured to be removably attached to the body. The head comprises an X-ray emitter positioned to emit X-ray radiation onto a geological sample material, an X-ray fluorescence detector configured to detect X-ray fluorescence emitted from the geological sample material, and an output port through which helium may be emitted onto the geological sample material. The head is configured such that X-ray radiation emitted from the X-ray emitter is incident directly on the geological sample material without being transmitted through any solid material between the X-ray emitter and the geological sample material.

The XRF unit according may also include an attachment portion mechanically attached to the head, a first passage formed in the head and a second passage, corresponding to the first passage, formed in the attachment portion. The first passage and the second passage, together, form a conduit for helium to pass therethrough between the output port and the geological sample material. The head may be configured to detect sodium in the geological sample material.

According to an aspect of another exemplary embodiment, a method of determining a location of recoverable hydrocarbons in a reservoir, includes: placing a plurality of geological sample materials, obtained within the reservoir, into a plurality of chambers formed within a tray; measuring a salinity, and/or other elemental properties of the plurality of geological sample materials. The measuring the salinity of the plurality of geological sample materials may comprise: positioning the tray with respect to an X-ray radiation emitter such that a first geological sample material disposed in a first concave chamber is irradiated by X-ray radiation emitted from the X-ray radiation emitter; irradiating the first geological sample material with the X-ray radiation emitted from the X-ray radiation emitter; detecting, with an X-ray fluorescence detector, X-ray fluorescence emitted from the first geological sample material; positioning the tray with respect to the X-ray radiation emitter such that a second geological sample material disposed in a second concave chamber is irradiated by X-ray radiation emitted from the X-ray radiation emitter; irradiating the second geological sample material with the X-ray radiation emitted from the X-ray radiation emitter; detecting, with the X-ray fluorescence detector, X-ray fluorescence emitted from the second geological sample material; outputting data of the X-ray fluorescence emitted by the first geological sample material and by the second geological sample material to a processor; and calculating, by the processor, a salinity of the first geological sample material and a salinity of the second geological sample material based on the data of the X-ray fluorescence output to the processor. The method additionally includes determining the location of recoverable hydrocarbons in the reservoir based on the salinity of the first geological sample material and the salinity of the second geological sample material.

The method may further include measuring an abundance of recoverable hydrocarbons in the plurality of geological sample materials, and the determining the location of recoverable hydrocarbons in the reservoir may be further based on the abundance of recoverable hydrocarbons in the geological sample materials. The measuring the abundance of recoverable hydrocarbons may include: positioning the tray with respect to a second sensor; detecting, by the second sensor, one or more properties of the first geological sample material and the second geological sample material; outputting data of the one or more properties of the first geological sample material and the second geological sample material to the processor; calculating, by the processor, the abundance of recoverable hydrocarbons in the first geological sample material and the second geological sample material based on the data of the one or more properties of the first geological sample material and the second geological sample material. The second sensor may be a spectrometer configured to measure a relative absorption of light to determine the presence of hydrocarbons, and the of the first geological sample material and the second geological sample material may be a light absorption of the first geological sample material and the second geological sample material. The spectrometer may be configured to measure a relative absorption of light in a range of wavelengths of about 1710 nm, about 1910 nm and/or about 2450 nm to determine the presence of hydrocarbons. The spectrometer may be a short-wave infrared (SWIR) spectrometer, a visible light spectrometer, or a passive gamma spectrometer. The spectrometer may be an imaging, line scanning, or point spectrometer. The spectrometer may utilize any one of prism, diffraction grating, and interferometer acquisition techniques.

BRIEF DESCRIPTION OF THE DRAWINGS

The above and/or other aspects will become apparent and more readily appreciated from the following description of example embodiments, taken in conjunction with the accompanying drawings in which.

DETAILED DESCRIPTION

Figure 1:
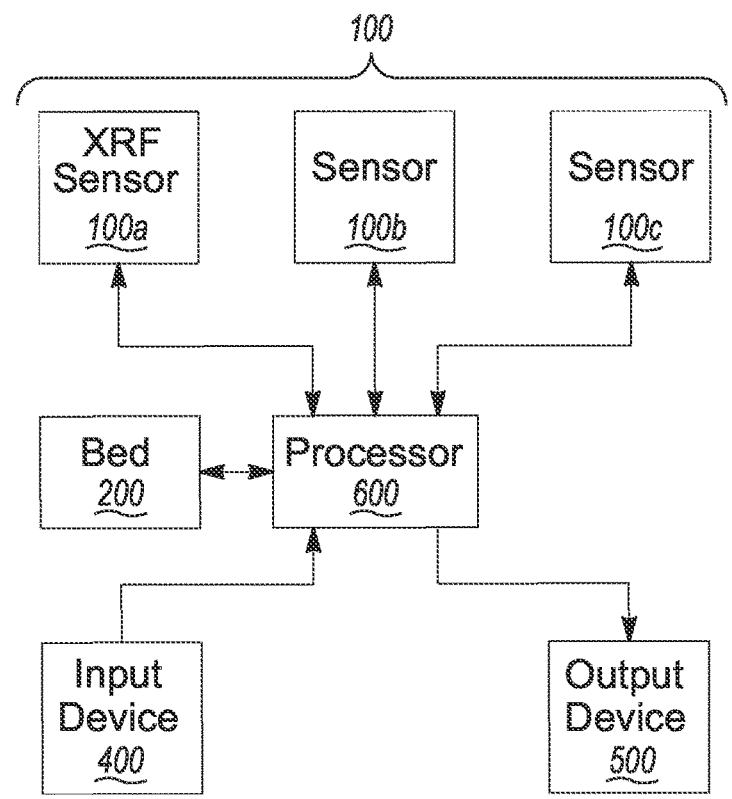
FIG. 1 is a schematic block diagram of a multi-component sample-scanning system according to an exemplary embodiment.

Reference will now be made in detail to exemplary embodiments which are illustrated in the accompanying drawings, wherein like reference numerals refer to like elements throughout. In this regard, the exemplary embodiments may have different forms and may not be construed as being limited to the descriptions set forth herein.

It will be understood that the terms "include," "including", "comprise, and/or "comprising," when used in this specification, specify the presence of stated features, integers, steps, operations, elements, and/or components, but do not preclude the presence or addition of one or more other features, integers, steps, operations, elements, components, and/or groups thereof.

It will be further understood that, although the terms "first," "second," "third," etc., may be used herein to describe various elements, components, regions, layers and/or sections, these elements, components, regions, layers and/or sections may not be limited by these terms. These terms are only used to distinguish one element, component, region, layer or section from another element, component, region, layer or section.

As used herein, the term "and/or" includes any and all combinations of one or more of the associated listed items. Expressions such as "at least one of," when preceding a list of elements, modify the entire list of elements and do not modify the individual elements of the list. In addition, the terms such as "unit," "-er (-or)," and 'module" described in the specification refer to an element for performing at least one function or operation, and may be implemented in hardware, software, or the combination of hardware and software.

Various terms are used to refer to particular system components. Different companies may refer to a component by different names—this document does not intend to distinguish between components that differ in name but not function.

Details of these exemplary embodiments that are obvious to those of ordinary skill in the technical field to which these exemplary embodiments pertain may not be described herein in detail.

One or more exemplary embodiments provide systems, devices, methods and computer program products for fully- and partially-automated analysis of soil and other geological samples including solids, fluids, and fluid-solid mixtures, and may include single- and multi-stage components and/or material analysis devices, and sample material holders such as trays.

Figure 2:
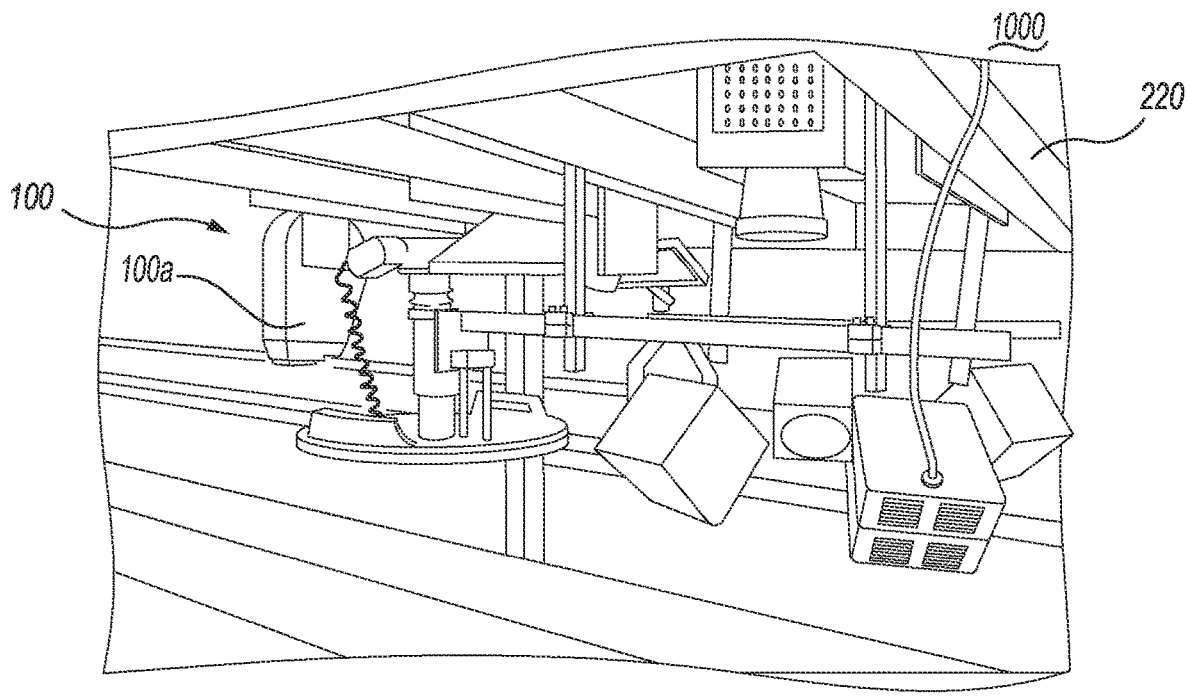
FIG. 2 is a perspective view of a multi-component sample-scanning system according to an exemplary embodiment.
Figure 3:
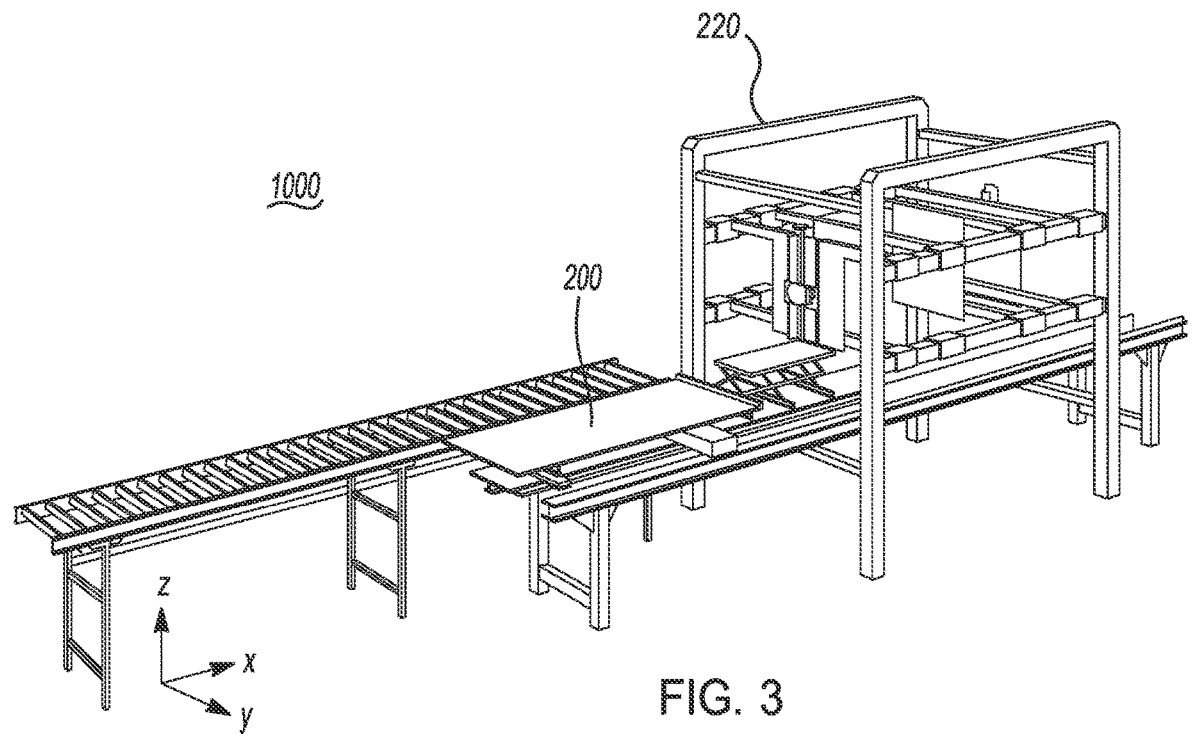
FIG. 3 is another perspective view of a multi-component sample-scanning system according to an exemplary embodiment.

FIGS. 1-3 illustrate a multi-component sample scanning system 1000 according to an exemplary embodiment.

As shown in FIG. 1, the system 1000 may include a plurality of sensors 100, one or more processors 600, a visual display, or other output device 500 and an input device 400 connected to the processor 600.

As will be apparent to one of skill in the art, the system 1000 can be provided in any of a very wide variety of forms, using a wide variety of type(s) and combination(s) of devices, components, and subsystems. The examples described herein are meant to be exemplary and not in any way limiting.

The processor(s) 600 may include any suitable general and/or specific-purpose processing unit(s), microprocessors, graphics processing units, digital signal processors, or any electromagnetic or other suitable digital signal processor, as would be understood by one of skill in the art.

The input device 400 can, for example, include one or more of a locally-connected keyboard, a keypad, a pointing device, and the like; and/or remotely-connected stand-alone computers such as laptops, desktops, notebooks, tablets, any mobile or networked computing device, and/or any other signal-generating device(s) suitable for providing control and/or other input commands to, and/or otherwise interacting with the processor 600 and associated devices.

The output device 500 may include any output device consistent with the purposes disclosed herein, including for example liquid-crystal displays (LCDs), light-emitting diode (LED) displays, cathode ray tube (CRT) displays, printer(s), audio speakers, and/or any other display device(s) suitable for use in displaying or otherwise reviewing, memorializing, or considering data in accordance with the purposes disclosed herein.

Devices, such as the sensors 100, bed 200, input device 400, and output device 500, connected to the processor(s) 600 may be connected to the processor(s) 600 locally or remotely via a physical line or network, such as a wireless local area network (WLAN).

The system 1000 may further include one or more memories (not shown).

The sensors 100 are each configured to provide signals representing various physical attributes of soil and/or geological sample materials, useful in their analysis to determine, for example, various aspects of their composition. FIG. 1 illustrates three sensors: an XRF unit 100a, and additional sensors 100b and 100c. However, greater than or fewer than three sensors may be included in the system 1000, and the three sensors illustrated in FIG. 1 are merely exemplary. The XRF sensor 100a may be, for example, a fast-flooded XRF sensor. The sensors 100 may further include one or more of a spectroscope, for example a short-wave infrared (SWIR) spectroscope, a visible light spectroscope, or a passive gamma spectroscope; a photosensitive camera, for example, an ultra-high resolution camera; a confocal laser; a microscope; a core gamma logger; a micro-lidar sensor; and a pressure decay sensor.

The processor(s) 600 is configured, for example by executing software instructions stored on a non-volatile memory, to receive input command signals generated by a user of the system 1000, and/or accessed in volatile or persistent memory, and to use such input signals to generate command signals suitable for use by one or more motors, hydraulic actuators, and/or other motive devices in moving each of the plurality of sensors 100 into an analysis position, relative to one or more of a plurality of samples, in accordance with either or both of predetermined sequence(s) and specific commands entered by an operator of the system 1000. The processor(s) 600 may additionally generate signals useful for controlling the sensors 100 to conduct analysis of the sample materials in such predetermined or specifically-commanded sequence.

As best shown in FIG. 2, the system 1000 comprises at least one frame 220 on which a bed 200 is received. The bed 200 may support the sample materials and may be moveable, as controlled manually or in accordance with commands generated by the processor(s) 600 or other device(s), to place sample materials in analysis positions with respect to the sensors 100. The bed 200 may be moveable in x- and y-directions, as shown in FIG. 3. In certain embodiments, the bed 200 may additionally be moveable in the z-axis direction, towards and away from the sensors 100 positioned thereabove, as shown. In other words, one or both of the sensors 100 and the sample materials may be moved, manually or via the processor(s) 600 into the relative analysis position(s).

The bed 200 may thereby position a tray 300 in any desired position, such that a sensor 100 may efficiently and effectively analyze a batch of samples on the tray 300. In various exemplary embodiments, multiple sensors 100 are provided, in order to analyze a plurality of trays 300 of sample materials simultaneously.

According to one or more exemplary embodiments, webcams and/or other optical devices may be positioned around the system 1000 and may obtain meta-data and aid in performance of quality control.

Figure 4A:
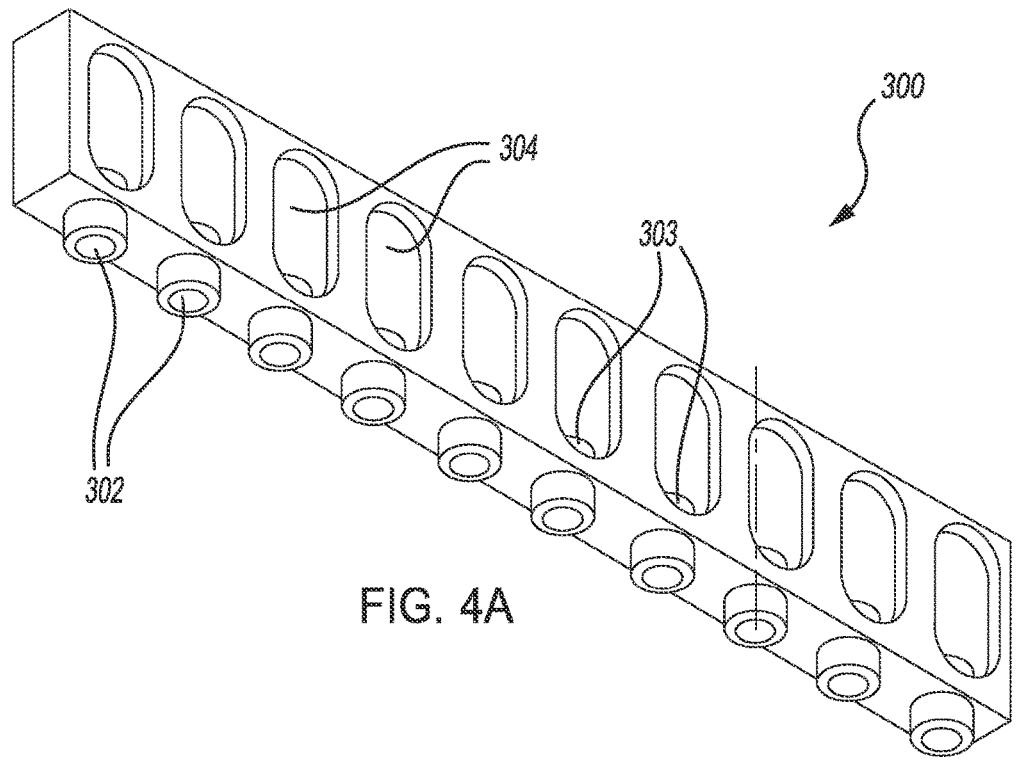
FIGS. 4A and 4B are perspective views of a multi-chamber sample tray according to an exemplary embodiment.
Figure 4B:
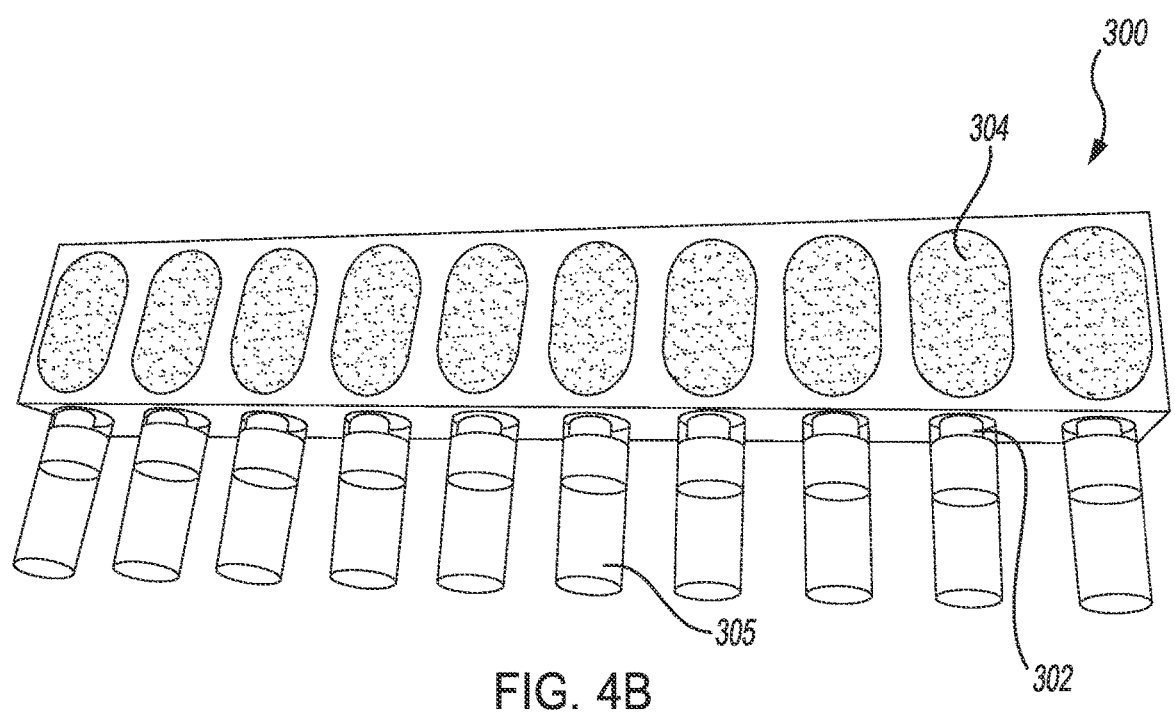
Figure 4C:
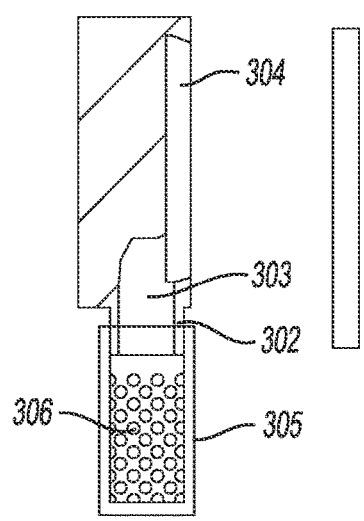
FIGS. 4C, 4D, and 4E are sectional views of the sample tray of FIGS. 4A and 4B.
Figure 4D:
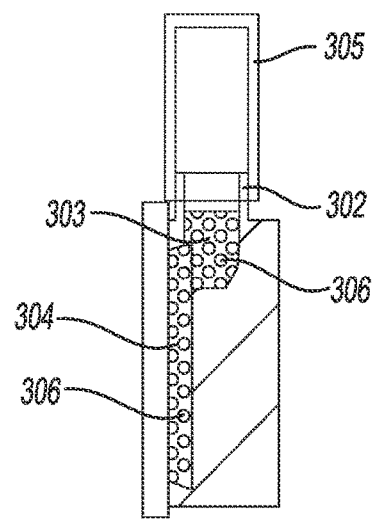
Figure 4E:
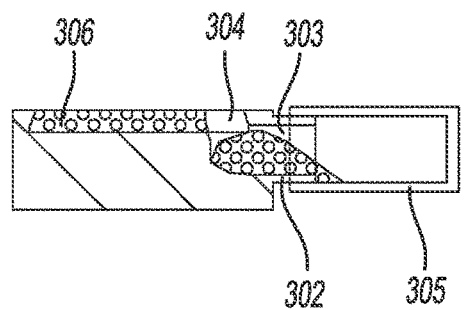

FIGS. 4A and 4B illustrate a sample tray 300 which holds sample materials 306 for simultaneous or sequential analysis by one or more of the sensors 100, according to an exemplary embodiment. The sample tray 300 may be supported by the bed 200. FIGS. 4C, 4D, and 4E are sectional views of the sample tray 300.

The sample tray 300 is configured to hold multiple geologic samples, simultaneously, in a plurality of sample chambers 304. Such samples may be from a single sample set, such as various portions of a single core sample, or from a plurality of generally unrelated sample sets, such as geographically-dispersed samples. The tray 300 may be 3D printed and may be made of aluminum or another metal or plastic. However, it is possible that a plastic tray will reflect light that undesirably interferes with a sensor 100, such as a short wave hyperspectral sensor, used in analysis of the sample materials 306 in the tray. The tray 300 also includes ports 302, respectively associated with the chambers 304, such that each port 302 is in communication with the interior of a chamber 304. Each port 302 is configured to be attachable to a sample vial 305. A passage 303 provides communication between the interior of the chamber 304 and the port 302, such that sample material 306 may move between the vial 305 attached opt the port 302 and the interior of the chamber 304.

FIG. 4C shows a sectional view of a single chamber 304, passage 303, and port 302 of the tray 300 and a vial 305 attached to the port 302. The tray 300 may additionally include a removable lid 350, associated with each chamber 304, as shown. FIG. 4C illustrates a state in which the vial 305 is attached to the port 302 by friction, and the sample material 306 is disposed within the vial 305. According to an exemplary aspect, the port 302 may include threading on its interior surface such that a via 1305, including its own threading, may be screwed onto the port 302. Alternately, the port 302 may be configured to be attached to a vial 305 by any of a variety of other mechanisms, as would be understood by one of skill in the art.

FIG. 4D illustrates a state in which the tray 300 and the vial 305 have been turned such that the sample material 306 previously within the vial 305 is pulled into the chamber 304 by gravity. As shown, some extra sample material 306 remains within the passage 303. The lid securely seals the upper, open side of the chamber 304. The lid XX may be mechanically attached to the tray 300 in any of a variety of manners, so long as the lid XX is removable, and, when attached to the tray 300, seals the chamber 304 so that none of the sample material 306 is lost.

FIG. 4E illustrates a state in which the tray 300 and the vial 305 have been turned such that the tray 300 is in a horizontal position and the lid XX has been removed therefrom. The vial 305 may be attached to the port 302, such that when the tray 300 is in the horizontal position, a label on the vial 305 faces upward so as to be readable and/or scannable for purposes of metadata capture. The area and depth of the chambers 304 may be determined, as would be understood by one of skill in the art, in accordance with the samples to be held therein so that the chamber 304 may be entirely filled with the sample material 306 with some extra material to block the passage 303 opening at a minimum depth of about 5 mm. The passage 303 between the port 302 and the chamber 304 may be configured and angled with an appropriately-sized opening so as to allow the sample material 306 to flow back and forth smoothly when tilted, but not when in the horizontal position, as shown in FIG. 4E. The passage 303 may be of sufficient length, relative its width, so that any light reflected by a vial 305 attached thereto is not incident through the passage 303 to thereby interfere with the signal from a sensor 100. The port 302 may be substantially cylindrical and an external diameter of the port 302 must be sized such that sufficient friction is provided between the port XX and the vial 305 attached thereto to hold the vial 305 in place on the port 302.

As shown in FIGS. 4C through 4E, a sample material 306 may be placed within a vial 305 which is attached to a port 302 of the tray 300. When one or more vials 305, each holding sample material 306, are attached to respective one or more ports 302 of the tray 300, the tray 300 and vial(s) 305 may be moved so that the sample material 306 in a vial 305 is transferred into a corresponding chamber 304 through the port 302 and passage 303. The tray 300 may then be moved into the horizontal position, as shown in FIG. 4E, for scanning by the sensors 100. Once in the chamber 304, the sample material 306 may then be transferred back into the vial 305, via the passage 303 and the port 302. The sample material 306 in the vial 305 may then be subjected to storage and/or further analysis. As would be understood by one of skill in the art, while a sample material 306 may be positioned for analysis by a sensor 100 without use of a tray 300, the use of the tray 300 may make the process of scanning and retaining the sample material 306 substantially easier and more effective, as it may be both easier to collect, handle, and store the sample material 306, using a tray 300, without losing or adulterating the sample material 306.

Figure 5C:
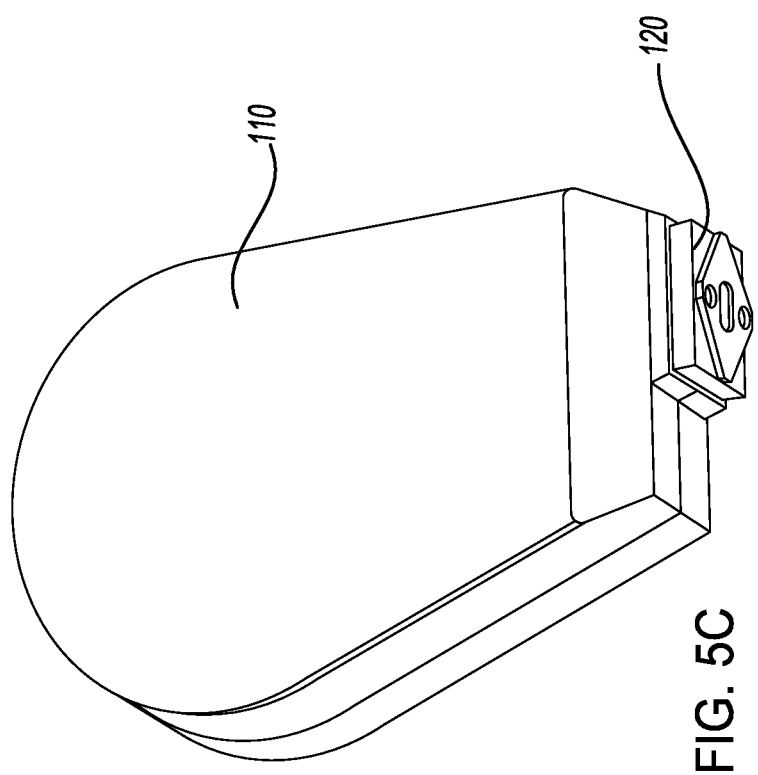
FIG. 5C is a perspective view of the XRF sensor body of FIG. 5A with a head attached thereto.
Figure 5A:
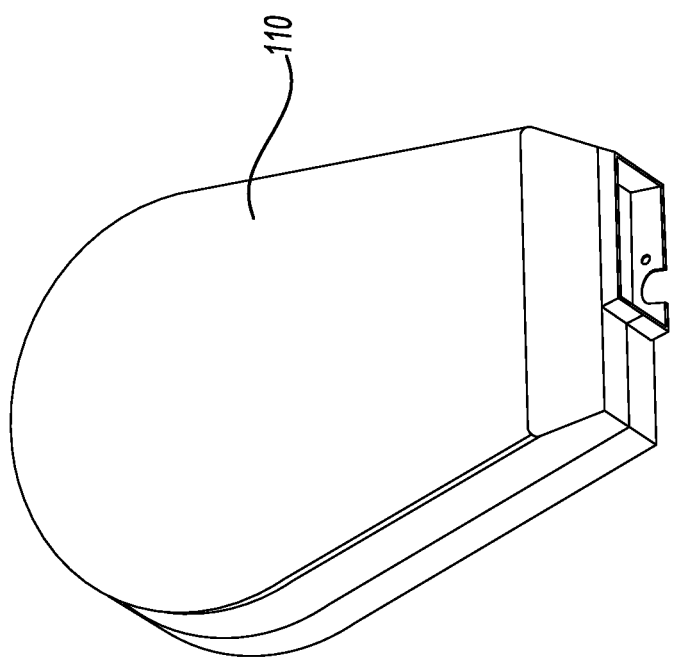
FIG. 5A is a perspective view of an XRF sensor body without a head.
Figure 5B:
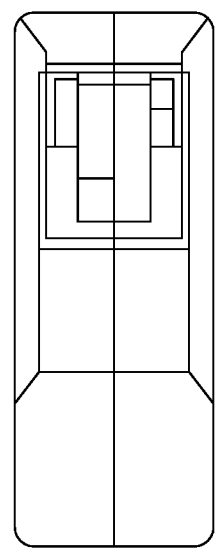
FIG. 5B is a bottom view of the XRF sensor body of FIG. 5A without the head.

FIG. 5A is a perspective view of an XRF sensor body without a head, FIG. 5B is a bottom view of the XRF sensor body of FIG. 5A without the head; and FIG. 5C is a perspective view of the XRF sensor body of FIG. 5A with a head attached thereto.

An XRF sensor 100a, as shown in FIGS. 5A-5C includes a body 110 and an XRF head 120, which may be removeably attached to the body 110.

Figure 6A:
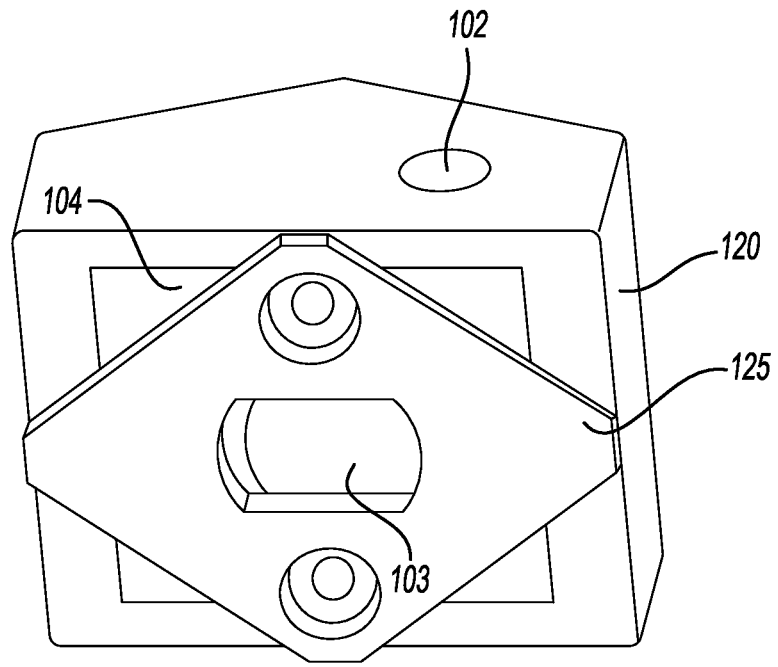
FIGS. 6A-6C are perspective views of an exemplary head of the x XRF sensor of FIG. 5C.
Figure 6B:
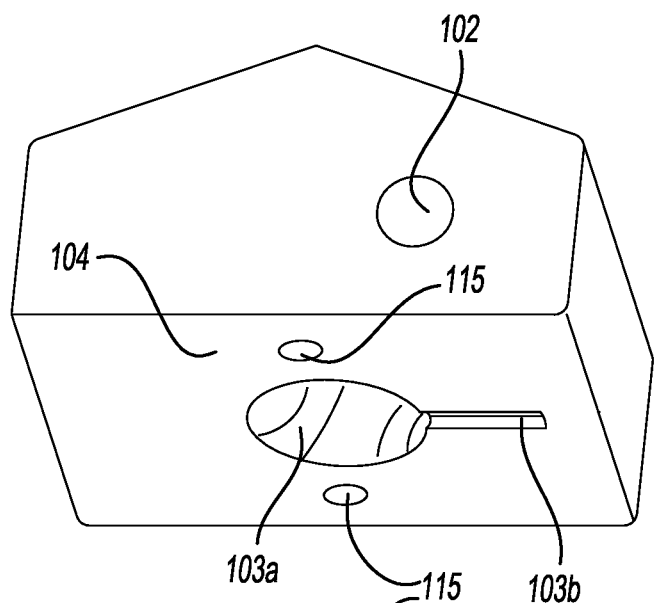
Figure 6B:
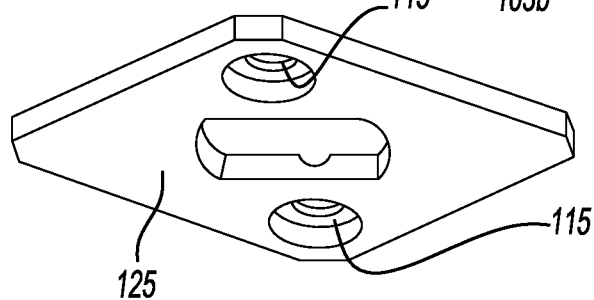
Figure 6C:
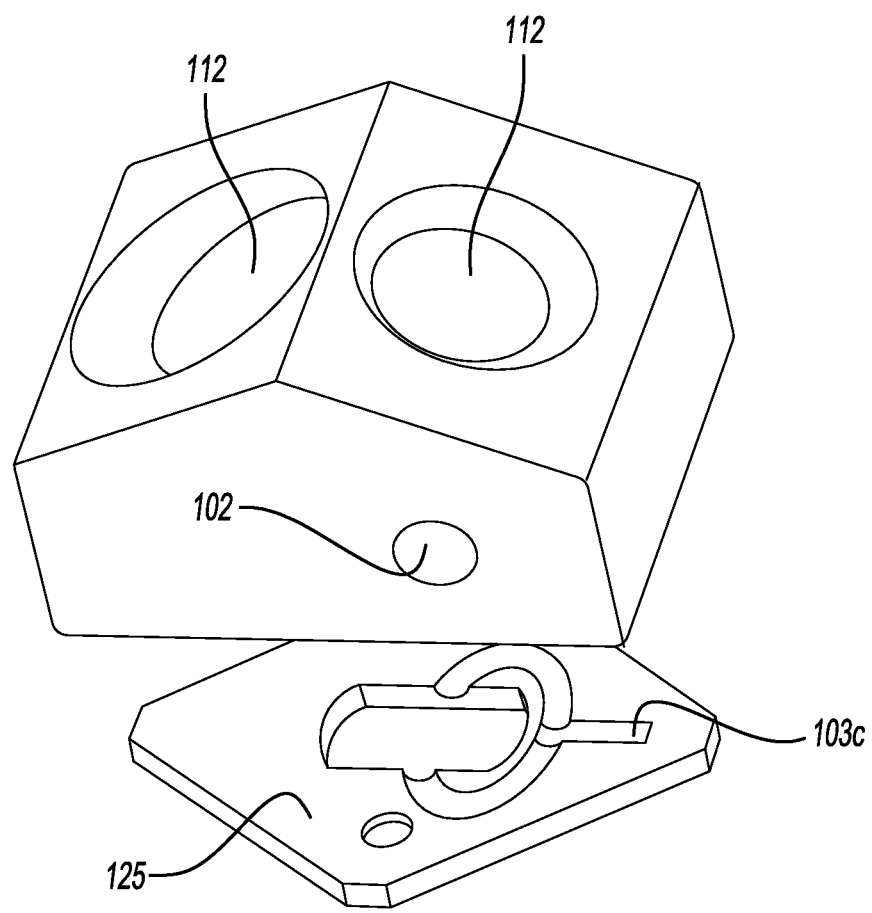
Figure 6D:
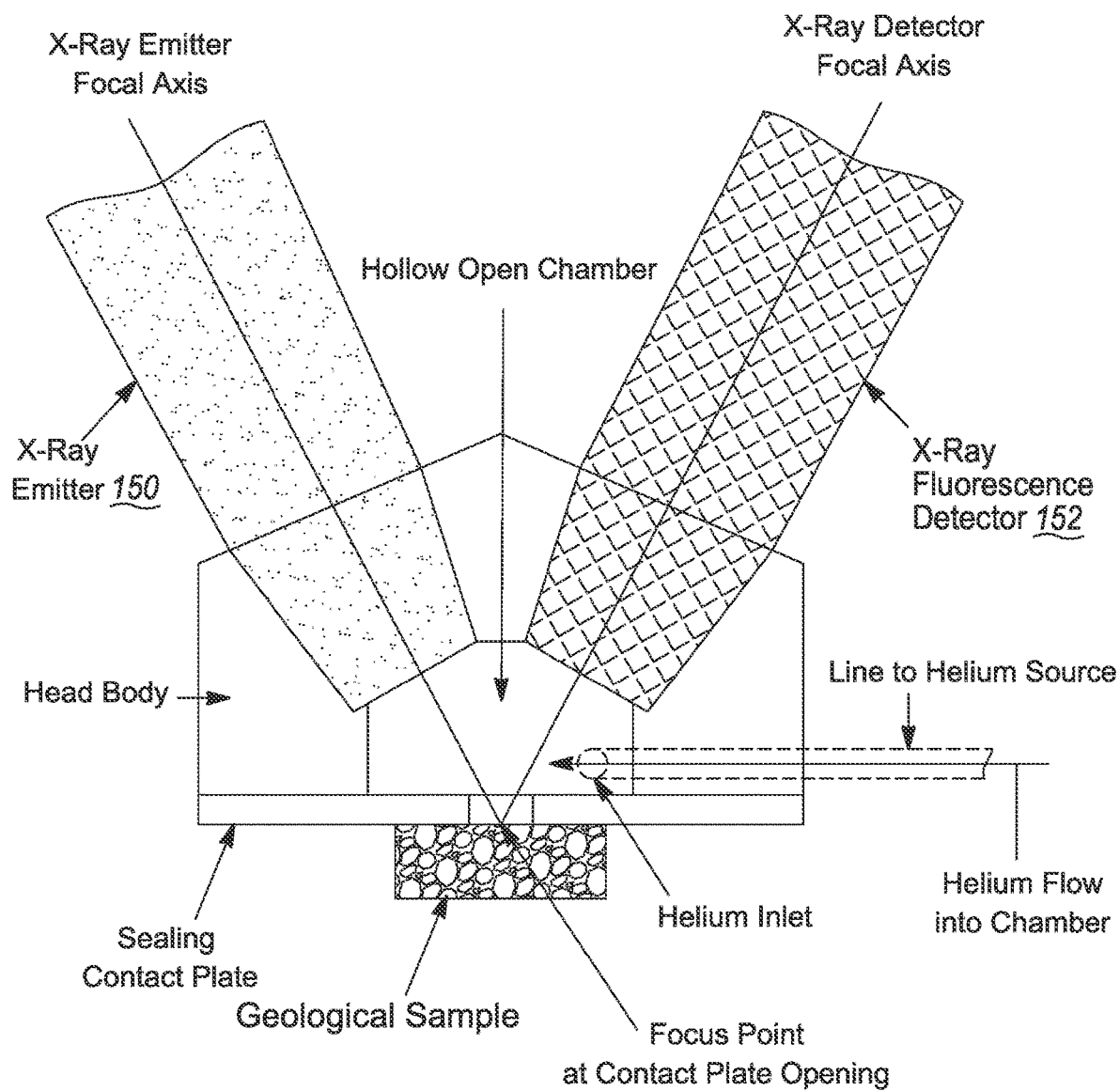
FIG. 6D is a cross-sectional view of the exemplary head.

Exemplary embodiments of the XRF head 120 are shown in FIGS. 6A-6D. As best shown in FIG. 6D, the XRF head 120 includes an x-ray emitter 150 and an x-ray fluorescence detector 152 which may seal holes 112 in the body 110 of the XRF head 120, as shown in FIG. 6C. The XRF head 120 includes an opening 102 through which helium and/or other substances may be introduced to the XRF head 120; and an opening 103 through which the helium and/or other substances may be transmitted from the head to the sample material 306. The XRF head 120 may include an attachment portion 125 which is attachable to the body 110 of the XRF head 120 by bolts threaded through bolt holes 115 or by another mechanical means as would be understood by one of skill in the art. Corresponding passages 103b and 103c in the body 110 of the XRF head 120 and in the attachment portion 125 guide the helium and/or other substances from the XRF head 120 to the sample material 306 in order to facilitate XRF analysis. A protective film 104 may be disposed between the body 110 of the XRF head 120 and the attachment portion 125. Related art XRF units commonly include a window or lens, through which the detection fluorescence must be transmitted, in order to protect the delicate detector. Unfortunately, such a window or lens often affects the detected signal. Therefore, such a window or lens may be omitted from the XRF head 120 according to an exemplary aspect. Thus, there is nothing in the way of the fluorescence signal from the sample material 306 being incident on the detector. The omission of the window or lens is possible because the contents of the detector are otherwise protected by having the XRF sensor 100a mounted on a rail or linkage arm of the system 1000, such that the rail or linkage arm maintains the XRF sensor 100a in a vertical alignment respective to the horizontal surface to be scanned. In view of this maintained vertical alignment, and the tray 300, as described above, which enables sample materials 306 to fill the chambers 304 and provide a flush horizontal surface to be scanned, there is little concern that the sample material 306 will undesirably enter the detector and cause damage.

Additionally, in view of the alignment that the system 1000 maintains between the sample tray 300 and the XRF sensor 100a, there is a single volume of space between the XRF sensor 100a and the sample material 306 so that helium or other gas can be released inside the XRF head 120 between the detector and the sample material 306. The helium may fill the entire space, such that the only way for the helium to escape is by pushing out the air and other gasses present in the sample material 306. Atmospheric argon and other gasses present in the sample material 306 may interfere with the XRF signal by masking the ability to detect light elements and reducing the quality of detection of other elements.

According to an exemplary aspect, an XRF head 120 is configured to detect sodium through the use of a vacuum or by flooding a sample material with a light gas, such as helium. Alternately, the XRF head 120 may be configured to detect chlorine via the use of a non-rhodium X-ray source.

In addition to the XRF sensor 100a, one or more additional sensors 100 may be used, including, but not limited to spectrometers of various types, including imaging, line scanning, and point spectrometers, spectrometers utilizing any of various acquisition techniques including, but not limited to, prisms, diffraction gratings, and interferometers (e.g. Fourier transforms). Another exemplary sensor 100 may be configured to measure the relative absorption of light in a range of wavelengths around 1710 nm, 1910 nm, and/or 2450 nm, in order to determine the presence of hydrocarbons.

Using the system 1000 equipped with the sensor(s) 100 and tray 300 according to one or more exemplary embodiments, measurements obtained by the sensors 100 may be used to identify continuous zones where the hydrocarbon abundance is above a technically/economically recoverable threshold; the salinity is below a technically/economically recoverable threshold; and the zone thickness is technically/economically drillable and completable. A salinity of a sample material can be determined based on fluorescence output by the sample material in response to irradiation of the sample material with X-ray radiation, as would be understood by one of skill in the art.

According to one or more exemplary embodiments, the data output from the scanner(s) 100 may also be compared to a library or database of rock properties to determine the categorization of the geological sample materials against known formations, lithology or other classifiers, including categorization of the sample materials into one or the classifiers known to exist in the reservoir.

According to one or more exemplary embodiments the data output from the scanner(s) 100 may be used to determine characteristics important to evaluating resources in place and selecting and optimizing recovery methods, including determining resource volumes, separating recoverable and non-recoverable resource volumes, and selecting engineering and completions methods and parameter for those methods, such as fluid and proppant types, rates, and pressures.

According to one or more exemplary embodiments, measurements obtained by the sensors 100 may be used to select drilling equipment and methods; completions equipment and methods; and/or production equipment and methods most appropriate for the targeted reservoir characteristics and size.

As would be understood by one of skill in the art, any of various aspects of exemplary embodiments described herein may be used in conjunction with any of a wide variety of data reduction, analysis, and other data processing techniques and applications thereof include, but are not limited to optimization of well or drilling paths, or other geosteering applications; maximization of recovery of data or materials from geological formations; machine vision d3etection of trace fossils and structural markers; big data mining for markers and correlations between geology and production; and machine learning optimization of tying cuttings to core data and other analysis workflows.

According to an exemplary embodiment, a method of analyzing geological sample material may include placing geological sample material in a chamber 304 of a plurality of chambers 304 of a sample tray 300. The sample material may be placed such that the chamber 304 is filled with the material and the material has a substantially planar upper, horizontal surface. The tray 300 (and/or the XRF sensor 100a) may be positioned with respect to an XRF sensor 100a, manually, by a fully- or semi-automatically controlled robotic bed 200, or by another mechanism as would be understood by one of skill in the art, such that the substantially planar upper surface of the material in the chamber 304 is in close or otherwise-desired proximity and orientation to the substantially vertically-oriented XRF sensor 100a. The tray 300 and/or XRF sensor 100a may be positioned such that a substantially enclose space is formed between the sample material and the detector of the XRF sensor 100a. The method may further include introducing helium, and/or another gas, into the space between the detector of the XRF sensor 100a and the sample material. The XRF sensor 100a is operated, in accordance with command signals generated by the processor(s) 600, to direct X-ray radiation onto the sample material and to detect fluorescence output from the sample material. The XRF sensor 100a outputs signals representing data regarding the detected fluorescence to the processor(s) 600. After analysis is performed by the XRF sensor 100a and/or processor(s) 600, the tray 300 may be repositioned such that analysis may be performed on the sample material by another sensor 100. Of course, analysis may also be performed on the sample material in the tray 300 prior to analysis by the XRF sensor 100a.

The material in the chamber 304 of the tray 300 may be transferred from the chamber 304 into a vial 305 attached to the tray 300. The tray 300 may be moved from a substantially horizontal position to a tilted position such that the sample material moves into the vial 305 via a port 302 in the tray 300 providing a transition between the chamber 304 and the vial 305.

Data from the analysis by one or more sensors 100 may be used for any of a number of purposes, including, but not limited to: determining a salinity of the sample materials and/or measuring an abundance of recoverable hydrocarbons in the sample material and thereby determining the location of recoverable hydrocarbons in a reservoir.

The systems and methods described herein may be embodied as software instructions on non-transitory computer-readable media.

It may be understood that the exemplary embodiments described herein may be considered in a descriptive sense only and not for purposes of limitation. Descriptions of features or aspects within each exemplary embodiment may be considered as available for other similar features or aspects in other exemplary embodiments.

While exemplary embodiments have been described with reference to the figures, it will be understood by those of ordinary skill in the art that various changes in form and details may be made therein without departing from the spirit and scope as defined by the following claims.

What is claimed is:

1. A geological analysis system comprising:
   at least one frame;
   a plurality of sensors, each sensor in the plurality of sensors mounted on the at least one frame, the plurality of sensors comprising an X-ray fluorescence (XRF) sensor comprising an X-ray emitter and an X-ray fluorescence detector;
   a sample tray comprising a plurality of concave chambers formed therein, wherein the sample tray is positionable in a first analysis position with respect to the XRF sensor such that a geological sample material disposed in one of the plurality of concave chambers is irradiated by X-ray radiation emitted from the X-ray emitter, and wherein the sample tray is positionable in a second analysis position with respect to a second sensor in the plurality of sensors such that the second sensor in the plurality of sensors may obtain data regarding the geological sample material; and
   a processor configured to:
      control a position of at least one of the sample tray and the plurality of sensors;
      control an operation of the plurality of sensors;
      output data received from the plurality of sensors; and
      effect semi-automatic or fully-automatic robotic positioning of one or both of the sample tray and the plurality of sensors with respect to the other.

2. The geological analysis system according to claim 1, wherein the processor is further configured to:
   measure a salinity of a plurality of geological sample materials placed within the plurality of concave chambers formed within the sample tray while the sample tray is the first analysis position by:
      positioning the sample tray with respect to the X-ray emitter such that a first geological sample material disposed in a first one of the plurality of concave chambers is irradiated by X-ray radiation emitted from the X-ray emitter;
      irradiating the first geological sample material with the X-ray radiation emitted from the X-ray emitter;
      detecting, with the X-ray fluorescence detector, X-ray fluorescence emitted from the first geological sample material;
      positioning the sample tray with respect to the X-ray emitter such that a second geological sample material disposed in a second one of the plurality of concave chambers is irradiated by X-ray radiation emitted from the X-ray emitter;
      irradiating the second geological sample material with the X-ray radiation emitted from the X-ray radiation emitter;
      detecting, with the X-ray fluorescence detector, X-ray fluorescence emitted from the second geological sample material;
      outputting data of the X-ray fluorescence emitted by the first geological sample material and by the second geological sample material to a processor; and
      calculating, by the processor, a salinity of the first geological sample material and a salinity of the second geological sample material based on the data of the X-ray fluorescence output to the processor; and
   determine a location of recoverable hydrocarbons in a reservoir based on the salinity of the first geological sample material and the salinity of the second geological sample material.

3. The geological analysis system according to claim 2, wherein the plurality of sensors comprise a second sensor comprising a spectrometer configured to measure a relative absorption of light to determine a presence of hydrocarbons.

4. The geological analysis system according to claim 3, wherein the processor is further configured to:
   measuring an abundance of recoverable hydrocarbons in the plurality of geological sample materials placed within the plurality of concave chambers formed within the sample tray while the sample tray is the second analysis position by:
      positioning the sample tray with respect to the spectrometer;
      detecting, by the spectrometer, an absorption of light of the first geological sample material and the second geological sample material;
      outputting data of the absorption of light of the first geological sample material and the second geological sample material to the processor;
      calculating, by the processor, the abundance of recoverable hydrocarbons in the first geological sample material and the second geological sample material based on the data of the absorption of light of the first geological sample material and the second geological sample material;
   wherein the processor is configured to determine the location of recoverable hydrocarbons in the reservoir is further based on the abundance of recoverable hydrocarbons in the first geological sample material and the second geological sample material.

5. An X-ray fluorescence (XRF) unit comprising:
   a body; and
   a head configured to be removably attached to the body, the head comprising:
      an X-ray emitter positioned to emit X-ray radiation onto a geological sample material;
      an X-ray fluorescence detector configured to detect X-ray fluorescence emitted from the geological sample material; and
      an output port through which helium may be emitted onto the geological sample material;
      wherein the head is configured such that X-ray radiation emitted from the X-ray emitter is incident directly on the geological sample material without being transmitted through any solid material between the X-ray emitter and the geological sample material.

6. The XRF unit according to claim 5, further comprising:
   an attachment portion mechanically attached to the head;
   a first passage formed in the head and a second passage, corresponding to the first passage, formed in the attachment portion, wherein the first passage and the second passage, together, form a conduit for helium to pass therethrough between the output port and the geological sample material.

7. The XRF unit according to claim 5, wherein the head is configured to detect sodium in the geological sample material.

8. A method of determining a location of recoverable hydrocarbons in a reservoir, the method comprising:
   placing a plurality of geological sample materials, obtained within the reservoir, into a plurality of concave chambers formed within a sample tray;
   measuring a salinity of the plurality of geological sample materials, the measuring the salinity of the plurality of geological sample materials comprising:
      positioning the sample tray with respect to an X-ray emitter such that a first geological sample material disposed in a first one of the plurality of concave chambers is irradiated by X-ray radiation emitted from the X-ray emitter;
      irradiating the first geological sample material with the X-ray radiation emitted from the X-ray emitter;
      detecting, with an X-ray fluorescence detector, X-ray fluorescence emitted from the first geological sample material;
      positioning the sample tray with respect to the X-ray emitter such that a second geological sample material disposed in a second one of the plurality of concave chambers is irradiated by X-ray radiation emitted from the X-ray emitter;
      irradiating the second geological sample material with the X-ray radiation emitted from the X-ray emitter;
      detecting, with the X-ray fluorescence detector, X-ray fluorescence emitted from the second geological sample material;
      outputting data of the X-ray fluorescence emitted by the first geological sample material and by the second geological sample material to a processor; and
      calculating, by the processor, a salinity of the first geological sample material and a salinity of the second geological sample material based on the data of the X-ray fluorescence output to the processor; and
   determining a location of recoverable hydrocarbons in the reservoir based on the salinity of the first geological sample material and the salinity of the second geological sample material.

9. The method according to claim 8, further comprising:
   measuring an abundance of recoverable hydrocarbons in the plurality of geological sample materials, the measuring an abundance of recoverable hydrocarbons comprising:
      positioning the sample tray with respect to a spectrometer configured to measure a relative absorption of light to determine a presence of hydrocarbons;
      detecting, by the spectrometer, an absorption of light of the first geological sample material and the second geological sample material;
      outputting data of the absorption of light of the first geological sample material and the second geological sample material to the processor;
      calculating, by the processor, the abundance of recoverable hydrocarbons in the first geological sample material and the second geological sample material based on the data of the absorption of light of the first geological sample material and the second geological sample material;
   wherein the determining the location of recoverable hydrocarbons in the reservoir is further based on the abundance of recoverable hydrocarbons in the first geological sample material and the second geological sample material.

10. The method according to claim 9, wherein the spectrometer is configured to measure a relative absorption of light in a range of wavelengths of about 1710 nm, about 1910 nm and/or about 2450 nm to determine the presence of hydrocarbons.

11. The method according to claim 10, wherein the spectrometer is a short-wave infrared (SWIR) spectrometer, a visible-light spectrometer, or a passive gamma spectrometer.

12. The method according to claim 10, wherein the spectrometer is an imaging spectrometer, a line-scanning spectrometer, or a point spectrometer.

13. The method according to claim 10, wherein the spectrometer utilizes any one of a prism, a diffraction grating, and an interferometer.

* * * * *